United States Patent [19]

Schropp

[11] 4,310,676

[45] Jan. 12, 1982

[54] METHOD OF STABILIZING MONOMERIC ACRYLIC ACID ESTERS AGAINST PREMATURE POLYMERIZATION AND ESTERS THUS STABILIZED

[75] Inventor: Wilhelm K. Schropp, Weinheim, Fed. Rep. of Germany

[73] Assignee: BASF Aktiengesellschaft, Ludwigshafen, Fed. Rep. of Germany

[21] Appl. No.: 164,527

[22] Filed: Jul. 2, 1980

[30] Foreign Application Priority Data

Aug. 3, 1979 [DE] Fed. Rep. of Germany ....... 2931553

[51] Int. Cl.³ ............................................ C07C 67/62
[52] U.S. Cl. ....................................................... 560/4
[58] Field of Search .......................................... 560/4

[56] References Cited

U.S. PATENT DOCUMENTS 3,959,358  5/1976  Jursich .................................... 560/4

FOREIGN PATENT DOCUMENTS 1064845  4/1967  United Kingdom .

OTHER PUBLICATIONS

Ullmans Encyclopadie der Technischen Chemie, Band 14, 3rd Ed., p. 116, 1963.

*Primary Examiner*—G. T. Breitenstein
*Assistant Examiner*—Vera C. Clarke
*Attorney, Agent, or Firm*—Oblon, Fisher, Spivak, McClelland & Maier

[57] ABSTRACT

A mixture of phenothiazine and para-nitrosophenol is a particularly effective stabilizer against premature polymerization of monomeric esters of acrylic acid with alkanols of 1 to 8 carbon atoms.

3 Claims, No Drawings

METHOD OF STABILIZING MONOMERIC ACRYLIC ACID ESTERS AGAINST PREMATURE POLYMERIZATION AND ESTERS THUS STABILIZED

The present invention relates to the prevention of premature polymerization during the preparation, transportation and storage of monomeric acrylic acid esters, or of compositions containing such esters, by addition of phenothiazine and para-nitrosophenol.

Substantial quantities of acrylic acid esters, in particular methyl, ethyl, butyl and 2-ethylhexyl acrylate, are used for the preparation of polymers and copolymers. During the preparation, storage and transportation of these esters, premature polymerization must be prevented. If such premature polymerization occurs, reaction vessels, pipelines, distillation columns, condensers, storage vessels and the like are contaminated or blocked by viscous or tacky polymers which are difficult to remove, so that the affected installation must be completely or partially shut down, and cleaned. Dealing with such operating troubles is time-consuming and often very expensive, especially if the polymer formed can no longer be dissolved and must be removed mechanically instead. The distillation columns used for the purification of acrylic acid esters are particularly prone to the formation of polymer.

Furthermore, the heat of reaction liberated during premature polymerization can constitute a hazard in the storage of acrylic acid esters.

A plurality of compounds have been proposed for stabilizing acrylic acid esters, cf., for example, "Ullmanns Encyclopädie der technischen Chemie", 3rd edition, volume 14 (1963), page 116. Most commonly, phenols, especially hydroquinone and hydroquinone monomethyl ether, as well as aliphatic and aromatic amines, are used. Examples of amines are para-phenylene-diamine and its derivatives, and phenothiazine, which is employed successfully especially in the case of acrylic acid and acrylic acid esters. Phenol derivatives, such as para-nitrosophenol, have also occasionally been mentioned as stabilizers for acrylic acid esters (for example in British Pat. No. 1,064,845).

I have found, surprisingly, that a mixture of phenothiazine and para-nitrosophenol is a particularly effective stabilizer against premature polymerization of monomeric esters of acrylic acid with alkanols of 1 to 8 carbon atoms. The stabilizer mixture according to the invention is substantially more effective than are the individual components, and the effect is also greater than the sum of the effects of the components.

The stabilizer mixture is in most cases employed in a conventional manner, namely by dissolving the envisaged amount of the stabilizer components, separately or as a mixture, in the stirred acrylic acid ester. It is particularly advantageous to employ concentrated solutions of the stabilizers in the monomers and to add such solutions to the remaining monomers in the reaction vessels, distillation columns, condensers and the like. The solubility of phenothiazine (I) and para-nitrosophenol (II) in esters of acrylic acid with alkanols of 1 to 8 carbon atoms is sufficiently high to permit this procedure.

The effect of the stabilizer mixtures depends, in a conventional manner, on the concentration and temperature, ie. the induction period before polymerization starts increases with increasing amount of stabilizer mixture and decreases with increasing temperature. Concentrations of stabilizer mixture of as little as 1 ppm, or even less, based on the weight of monomer, are effective. For most applications, it is usual to employ concentrations of from 5 to 100 ppm, and at times even higher concentrations, of up to 1,000 ppm, may be chosen, especially if relatively high temperatures must be used. Though even higher doses are also effective, they are avoided, for economic reasons. Accordingly, the concentration of stabilizer mixture is in most cases from 1 to 100 ppm, based on monomer. Very good stabilization of monomeric acrylic acid esters is observed if the proportion of (I) in the mixture of (I) and (II) is from 80 to 20 percent by weight; in general, this proportion is from 70 to 30 percent by weight, and proportions of from 60 to 40 percent by weight are preferred. Frequently, about equal amounts by weight of the components are particularly effective.

The novel stabilizer mixtures lengthen the induction period of the polymerization of acrylic acid esters. The induction period, ie. the time from the start of the experiment up to when polymerization commences, can, for example, be measured simply by sealing the test mixtures into sample tubes, introducing these into an accurately controlled thermostatic bath and ascertaining, by occasionally turning the tubes, whether the sample is still mobile or has solidified as a result of polymerization.

The stability of the mixtures stabilized by the process according to the invention was assessed by making up at least four samples at each of the chosen stabilizer concentrations. The bath temperature was 80±0.5° C. in every case.

All the monomers used were purified by vacuum distillation to remove the storage stabilizer (=hydroquinone monomethyl ether); thereafter, the residual stabilizer content was less than 0.2 ppm.

Commercial stabilizers (I) (at least 99% pure) and (II) (about 83% pure, remainder water) were used.

To prepare the test solutions, the stabilizers were weighed out and dissolved in 1/10 of the requisite amount of acrylate. After having been stirred for one hour, the solutions were filtered and diluted.

EXAMPLE 1

Stabilization of methyl acrylate

TABLE 1

| Amount of (I) in ppm | Amount of (II) in ppm | Time up to commencement of polymerization (hours) |
|---|---|---|
| 4 | 1 | 12.5 |
| 3 | 2 | 18.5 |
| 2 | 3 | 15.0 |
| 1 | 4 | 6.1 |
| 30 | 20 | 326 |
| 20 | 30 | 309 |

Whilst stabilizer-free methyl acrylate is only stable for 1.9 hours, this period is increased to 6 hours and 3.2 hours by the addition of 5 ppm of (I) and 5 ppm of (II), respectively. However, these results are far exceeded if, whilst retaining the same total concentration, combinations of both stabilizers are employed. With 3 ppm of (I) and 2 ppm of (II), the shelf life achieved was more than three times as long as with 5 ppm of (I).

The same effect is also found at a total concentration of 50 ppm, as may be seen from the lower part of Table 1, the induction period for 50 ppm of (I) being 130 hours and for 50 ppm of (II) 68 hours.

EXAMPLE 2

Stabilization of ethyl acrylate

Virtually stabilizer-free ethyl acrylate has an induction period of 6 hours. With 10 ppm of (I) and 10 ppm of (II), the induction period is 260 hours. By contrast, 20 ppm of (I) alone gives an induction period of only 129 hours and 20 ppm of (II) alone an induction period of only 25 hours.

EXAMPLE 3

Stabilization of n-butyl acrylate

| Amount of (I) in ppm | Amount of (II) in ppm | Time up to commencement of polymerization (hours) |
| --- | --- | --- |
| 10 | 10 | 514 |
| 8 | 12 | 534 |
| 6 | 14 | 579 |
| 2 | 18 | 351 |

For comparison, the induction period for virtually stabilizer-free butyl acrylate is 10 hours, whilst it is 251 hours when using 20 ppm of (I) alone and only 49 hours when using 20 ppm of (II) alone.

EXAMPLE 4

Stabilization of 2-ethylhexyl acrylate

Virtually stabilizer-free 2-ethylhexyl acrylate has an induction period of 6 hours. 2-Ethylhexyl acrylate stabilized according to the invention with 2.5 ppm of (I) and 2.5 ppm of (II) polymerizes after 69 hours. For comparison, the induction period using 5 ppm of (I) alone is 37 hours and using 5 ppm of (II) alone it is 20.5 hours.

I claim:

1. A process for stabilizing monomeric esters of acrylic acid with alkanols of 1 to 8 carbon atoms against premature polymerization, which comprises admixing with said monomeric ester phenothiazine and para-nitrosophenol.

2. A process as claimed in claim 1, wherein from 1 to 100 ppm of a mixture of from 80 to 20 percent by weight of phenothiazine and from 20 to 80 percent by weight of p-nitrosophenol, the percentages being based on the stabilizer mixture, are added to the acrylic acid ester.

3. An ester of acrylic acid with an alkanol of 1 to 8 carbon atoms, which ester contains from 1 to 1,000 ppm of a mixture of from 80 to 20 percent by weight of phenothiazine and from 20 to 80 percent by weight of p-nitrosophenol, the percentages being based on the stabilizer mixture, as a stabilizer against premature polymerization.

* * * * *